(12) United States Patent
Sabin et al.

(10) Patent No.: US 10,507,270 B1
(45) Date of Patent: Dec. 17, 2019

(54) SURGICAL APPARATUS, SYSTEM AND METHOD

(71) Applicant: Fikst Product Development, Woburn, MA (US)

(72) Inventors: Paul C. Sabin, Needham, MA (US); James F. Biggins, Waltham, MA (US); Matthew Hanczor, Redding, CT (US); Andrew John Caunter, Hampton Falls, NH (US)

(*) Notice: Subject to any disclaimer, the term of this patent is extended or adjusted under 35 U.S.C. 154(b) by 556 days.

(21) Appl. No.: 15/067,692

(22) Filed: Mar. 11, 2016

Related U.S. Application Data

(60) Provisional application No. 62/131,924, filed on Mar. 12, 2015.

(51) Int. Cl.
| A61M 1/00 | (2006.01) |
| A61F 13/38 | (2006.01) |
| A61B 90/70 | (2016.01) |
| A61B 17/34 | (2006.01) |

(52) U.S. Cl.
CPC ......... *A61M 1/008* (2013.01); *A61B 17/3417* (2013.01); *A61B 90/70* (2016.02); *A61F 13/38* (2013.01); *A61B 2090/701* (2016.02)

(58) Field of Classification Search
CPC .... A61M 1/008; A61B 90/70; A61B 17/3417; A61B 2090/701; A61F 13/38
USPC ........................................................ 604/267
See application file for complete search history.

(56) References Cited

U.S. PATENT DOCUMENTS

| 2,644,234 A | 7/1953 | Scott |
| 3,169,528 A | 2/1965 | Knox |
| 3,324,855 A | 6/1967 | Heimlich |
| 3,394,702 A | 7/1968 | Heimlich et al. |
| 3,520,300 A | 7/1970 | Flower |
| 4,068,664 A | 1/1978 | Sharp et al. |
| 4,252,166 A | 2/1981 | Kozicki |
| 4,321,921 A | 3/1982 | Laszczower |
| 4,883,465 A | 11/1989 | Brennan |
| 4,935,006 A | 6/1990 | Hasson |
| 5,071,347 A | 12/1991 | McGuire |
| 5,094,616 A | 3/1992 | Levenson |
| 5,151,094 A | 9/1992 | Hanifi |
| 5,203,699 A | 4/1993 | McGuire |

(Continued)

FOREIGN PATENT DOCUMENTS

| EP | 1891997 A1 | 2/2008 |
| WO | 2014169135 A2 | 10/2014 |

*Primary Examiner* — Phillip A Gray
(74) *Attorney, Agent, or Firm* — Rhodes Donahoe, LLC; Robert V. Donahoe

(57) ABSTRACT

An apparatus is provided for use in combination with a surgical sponge assembly and a trocar including a cannula where the surgical sponge assembly includes a suction tube coupled to a sponge head. A body includes a proximal end, a distal end, and a first lumen and a second lumen that join one another to form a cavity. The first lumen and the second lumen are separated from one another by an interior wall that extends from the proximal end of the body to the cavity. The first lumen is sized and configured to allow an axial movement of the suction tube within the first lumen and the cavity is configured to store at least a portion of the sponge head. The apparatus is configured to allow the surgical sponge assembly to be moved from a retracted position to an extended position.

11 Claims, 11 Drawing Sheets

(56) References Cited

U.S. PATENT DOCUMENTS

| | | |
|---|---|---|
| 5,205,816 A | 4/1993 | Dodson |
| 5,310,406 A | 5/1994 | Sharpe |
| 5,437,651 A | 8/1995 | Todd et al. |
| 5,599,330 A | 2/1997 | Rainin |
| 5,628,735 A | 5/1997 | Skow |
| 5,649,902 A | 7/1997 | Yoon |
| 5,921,972 A | 7/1999 | Skow |
| 5,975,897 A | 11/1999 | Propp et al. |
| 6,068,477 A | 5/2000 | Mahlmann |
| 6,235,009 B1 | 5/2001 | Skow |
| 6,282,442 B1 | 8/2001 | DeStefano et al. |
| 6,565,544 B1 | 5/2003 | Rainin |
| 6,620,132 B1 | 9/2003 | Skow |
| 6,712,757 B2 | 3/2004 | Becker et al. |
| 7,175,594 B2 | 2/2007 | Foulkes |
| 7,699,831 B2 | 4/2010 | Bengston et al. |
| 2003/0130674 A1* | 7/2003 | Kasahara ......... A61B 17/00008 606/159 |
| 2011/0105842 A1 | 5/2011 | Fogel |
| 2011/0151405 A1 | 6/2011 | Dombrowski |
| 2011/0159457 A1 | 6/2011 | Offermann |
| 2014/0088529 A1* | 3/2014 | Bengtson ............ A61F 13/36 604/360 |

\* cited by examiner

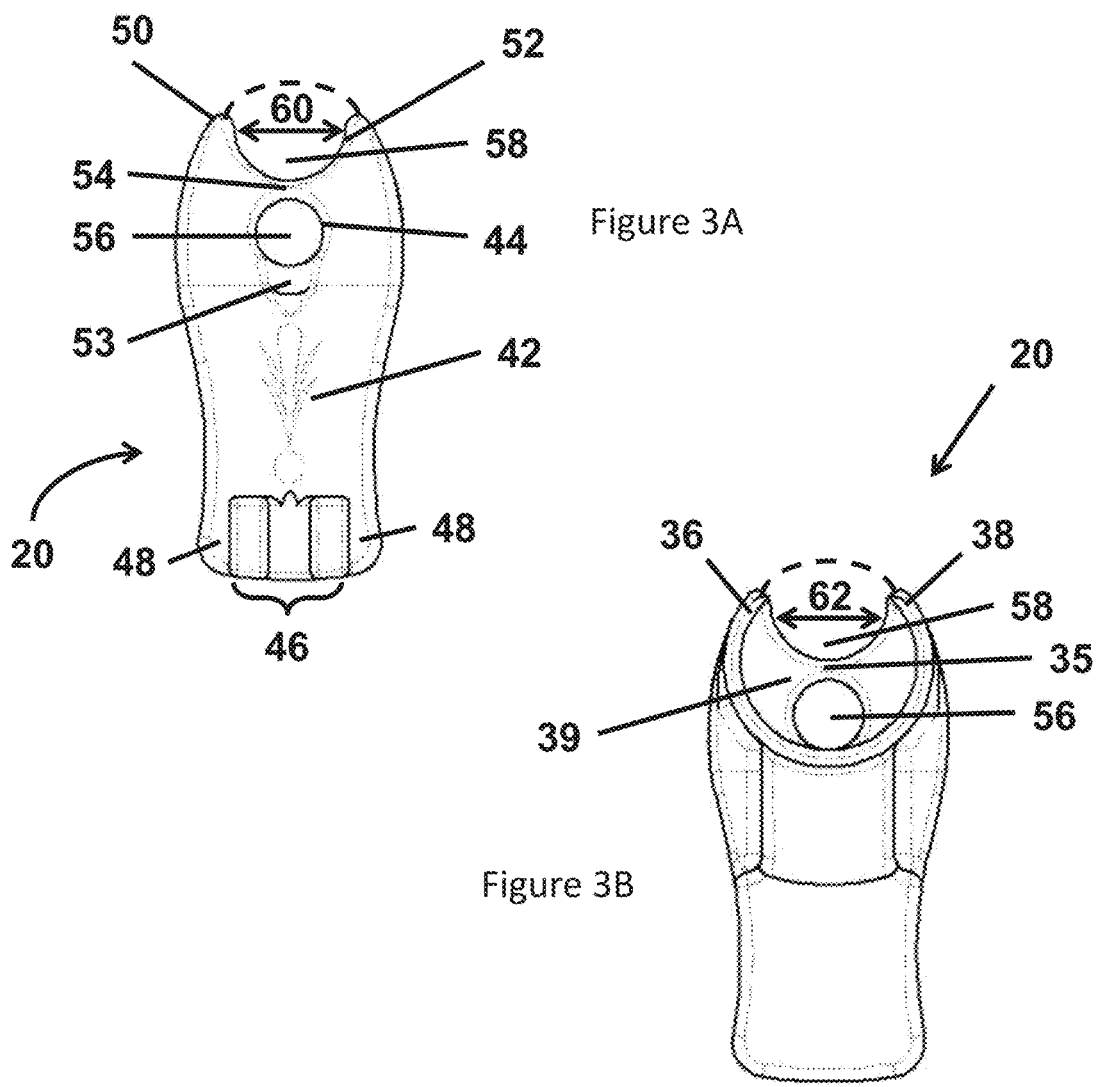

SURGICAL APPARATUS, SYSTEM AND METHOD

BACKGROUND OF INVENTION

1. Field of Invention

Embodiments of the invention generally relate to surgical instruments and methods of use, more specifically, at least one embodiment relates to apparatus, systems and methods employing a surgical sponge.

2. Discussion of Related Art

Because visual identification is crucial for decision making, surgeons spend significant time making sure that surgical sites are fluid free so they have good visibility. To achieve the preceding, surgical sponges are employed to absorb bodily fluids and other liquids in surgical procedures. Often, surgical sponges are employed with suction so that excess liquid is not only absorbed, but removed from the area. However, suction tubes have a tendency to draw delicate tissue within the tube from the area of the procedure. For example, pressure can spike upward at an inlet to a suction tube should the flow in the tube become occluded. Delicate tissue caught in the suction can get harmed, for example, if it is drawn in the tube during the pressure spike. Some approaches now draw suction through gauze to try to reduce the frequency of these events. While the use of gauze can assist, gauze is generally manufactured using an open weave that has a tendency to create lint. Lint is undesirable in a surgical site.

Sponges can quickly become saturated during surgical procedures. In addition, sponges can get left behind. The preceding can cause serious complications and great risk to the patient.

Trocars and other surgical instruments are employed to provide a port through which a surgeon gains access to a body cavity, for example, to perform surgery such as laparoscopic, arthroscopic and endoscopic procedures. Often, a trocar is used in minimally invasive procedures to minimize the size of incisions. Such approaches can allow a patient to recovery more quickly and experience less discomfort as a result of the procedure. FIGS. 1A and 1B illustrate one such prior art trocar 10. The trocar 10 includes a head 12 and a cannula 14 including a proximal end 15 and a distal end 17.

The trocar 10 provides a single lumen 16 through which surgical tools can be employed, for example, imaging equipment, equipment for making incisions, such as scalpels, equipment for gripping, such as forceps, stitching equipment and surgical sponges.

However, because they employ only a single lumen, current approaches make it difficult to simultaneously employ multiple surgical tools in a procedure. For example, a surgeon may find it nearly impossible to locate imaging equipment and a surgical sponge in the body cavity via a single trocar. Further, many common configurations of surgical sponges are difficult to insert and deploy via a trocar because of the limited dimensions and cylindrical shape of the port.

In addition, fluid can be left in the single lumen when a sponge is withdrawn. This excess fluid can impede the subsequent use of the same lumen for a different surgical tool. For example, the lens on imaging equipment can become contaminated with the excess fluid which can affect the quality of the images that are provided.

SUMMARY OF INVENTION

According to the various apparatus, system and methods described herein, a single lumen trocar is adapted to facilitate the use of a surgical sponge in a procedure via the trocar. In various embodiments, the apparatus also allows for the simultaneous use of a different surgical tool via the same trocar using a separate lumen.

In one aspect, an apparatus is provided for use in combination with a surgical sponge assembly and a trocar including a cannula where the surgical sponge assembly includes a suction tube coupled to a sponge head. In various embodiments, the apparatus includes a body configured to insert within the cannula. The body includes a proximal end, a distal end, and a first lumen and a second lumen that join one another to form a cavity. The first lumen and the second lumen are separated from one another by an interior wall that extends from the proximal end of the body to the cavity. The first lumen is sized and configured to allow an axial movement of the suction tube within the first lumen and the cavity is configured to store at least a portion of the sponge head. Further, the apparatus is configured to allow the surgical sponge assembly to be moved from a retracted position in which at least a portion of the sponge head is stored within the cavity and an extended position in which at least some of the portion of the sponge head stored within the cavity in the retracted position is located beyond the distal end of the body.

According to another embodiment, an adapter is provided for use with a trocar including a head, a seal located within the head and a cannula attached to the head. In various embodiments, the adapter includes a flange defining a first opening and a second opening, the flange configured to remain outside the cannula with the adapter disposed within the trocar; a neck including a proximal end attached to the flange, and a distal end, the neck having an outside diameter selected to engage the seal included in the trocar with the adapter disposed within the trocar; a body having a proximal end coupled to the distal end of the neck, a distal end that defines an opening located at a distal end of the adapter, an interior wall, and an open region located between the distal end of the interior wall and the distal end of the adapter; a first lumen extending from the first opening through the neck to a third opening located at a distal end of the interior wall, the first lumen located parallel to a longitudinal axis of the adapter and configured to receive at least a portion of a suction device including a surgical sponge and to allow axial movement of the at least the portion of the suction device within the first lumen; and a second lumen extending from the second opening through the neck to the distal end of the interior wall, the second lumen located parallel to the longitudinal axis of the adapter and configured to receive a surgical tool. According to further embodiments, the adapter is configured to allow the surgical sponge to be moved between a retracted position in which at least a portion of the sponge is located within the open region and an extended position in which the surgical sponge is located beyond the distal end of the adapter.

According to another aspect, a method of employing a suction device and a surgical tool via a single-lumen trocar is provided where the single-lumen trocar including a head, a seal located within the head and a cannula attached to the head. According to some embodiments, the method includes providing an adapter; locating the adapter within the cannula such that the neck engages the seal; moving the suction device in a distal direction by applying a force to a proximal end of the suction device in an axial direction to place the surgical sponge in the extended position such that the surgical sponge is located beyond a distal end of the cannula; and inserting the surgical tool within the second lumen to locate a distal end of the surgical tool beyond the distal end of the cannula.

According to still another aspect, a kit for use with a trocar assembly including a seal and a cannula is provided. According to some embodiments, the kit includes a surgical device including a tube coupled to a surgical sponge; and an adapter including a first lumen and a second lumen, the adapter including a body sized and configured to be received within the cannula, the first lumen and the second lumen extending from a proximal end of the adapter to a cavity located within the body. In a further embodiment, the first lumen is sized such that the tube can be slidably disposed within the first lumen, and the cavity is sized such that at least a portion of the surgical sponge can be slidably disposed within the cavity between a retracted position in which at least a portion of the sponge is located within the cavity and an extended position in which the surgical sponge is located beyond the distal end of the adapter.

According to yet another aspect, a method of assembling an adapter kit for use with a trocar is provided where the trocar includes a head, a seal located within the head and a cannula attached to the head. In some embodiments, the method includes providing an apparatus configured for use with a single lumen of the trocar, the adapter including a flange defining a first opening and a second opening, the flange configured to remain outside the cannula with the adapter disposed within the single lumen, a neck including a proximal end attached to the flange, and a distal end, the neck configured to engage the seal included in the trocar with the adapter disposed within the trocar; a body having a proximal end coupled to the distal end of the neck, and a distal end that defines an opening located at a distal end of the adapter, a first lumen extending axially from the first opening through the neck and to a cavity formed within the body, a second lumen extending axially from the second opening through the neck to the cavity; providing a suction device including a tube and a sponge assembly coupled to a distal end of the tube; sliding the tube within the first lumen, from the distal end of the first lumen, to move a proximal end of the tube beyond the first opening; and moving the proximal end of the tube axially to withdraw the tube through the first opening and locate the sponge assembly within the cavity.

According to another aspect, a surgical sponge assembly includes: a non-absorbent backing layer including an edge region and providing a first side of the surgical sponge assembly; an absorbent fiber layer including an edge region and providing a second side of the surgical sponge assembly; and a gauze layer located between the non-absorbent backing layer and the absorbent fiber layer, the gauze layer including an edge region. According to one embodiment, the absorbent fiber layer includes one of a medical tissue and a nonwoven-pressed pad to provide a substantially lint free absorbent material. In a further embodiment, the edge region of the non-absorbent backing layer, the edge region of the absorbent fiber layer and the edge region of the gauze layer are secured to one another using injected silicone.

According to another aspect a surgical tool includes a tube including a proximal end configured to couple to a source of suction, and a distal end; and a sponge assembly coupled to the distal end of the tube, the sponge assembly including a proximal end and a distal end. According to some embodiments, the sponge assembly includes a non-absorbent backing layer including a first edge region and a second edge; a gauze layer adjacent the non-absorbent backing layer and including a first edge region and a second edge; and an absorbent fiber layer adjacent the gauze layer and including a first edge region and a second edge region. In one embodiment, the first edge region of the backing layer, the first edge region of the gauze layer and the first edge region of the absorbent fiber layer are secured to one another using a first injected silicone rib, the second edge region of the backing layer, the second edge region of the gauze layer and the second edge region of the absorbent fiber layer are secured to one another using a second injected silicone rib, the first injected silicone rib and the second injected silicone rib meet at a proximal end of the sponge assembly to secure the sponge assembly to the tube, and the distal end of the tube is located within the sponge assembly between the gauze layer and the absorbent fiber layer with the respective first edge regions secured to one another and the respective second edge regions to one another.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 3A is a plan view of a proximal end of the adapter illustrated in FIG. 2;

FIG. 3B is a plan view of a distal end of the adapter illustrated in FIG. 2;

DETAILED DESCRIPTION

Figure 1A:
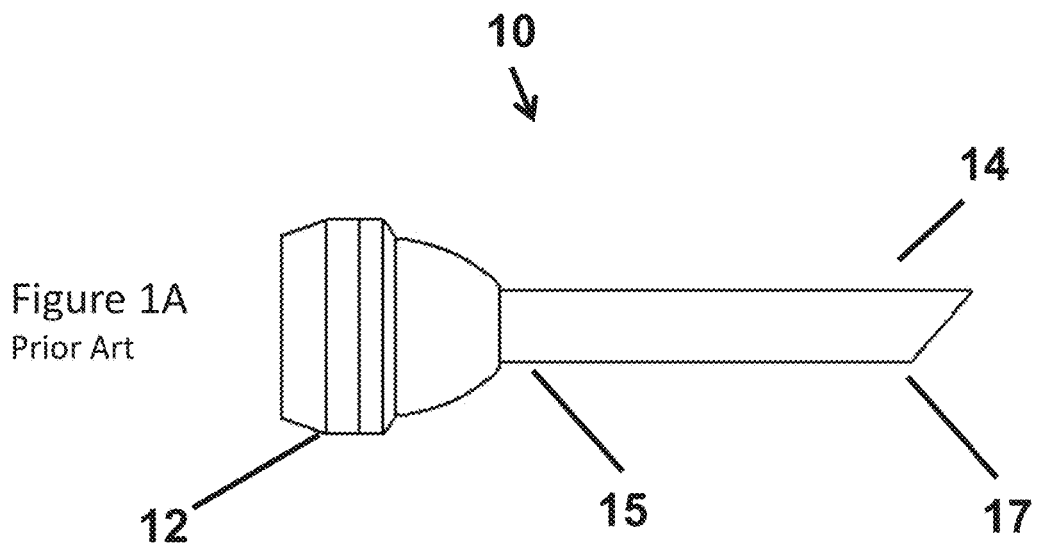
FIG. 1A is a side view of a trocar according to the prior art.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

Figure 1B:
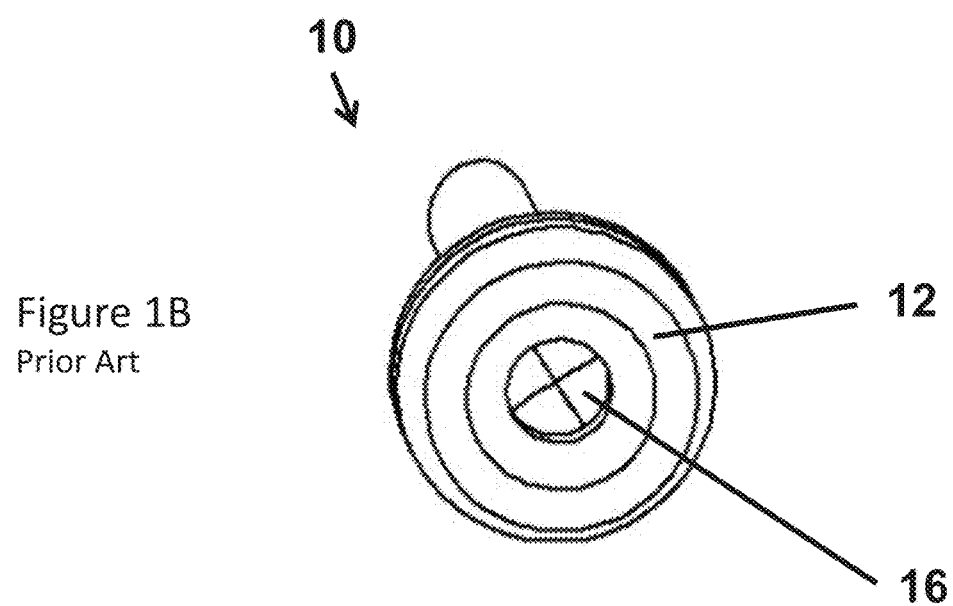
FIG. 1B is an end view of the trocar illustrated in FIG. 1A.
Figure 2:
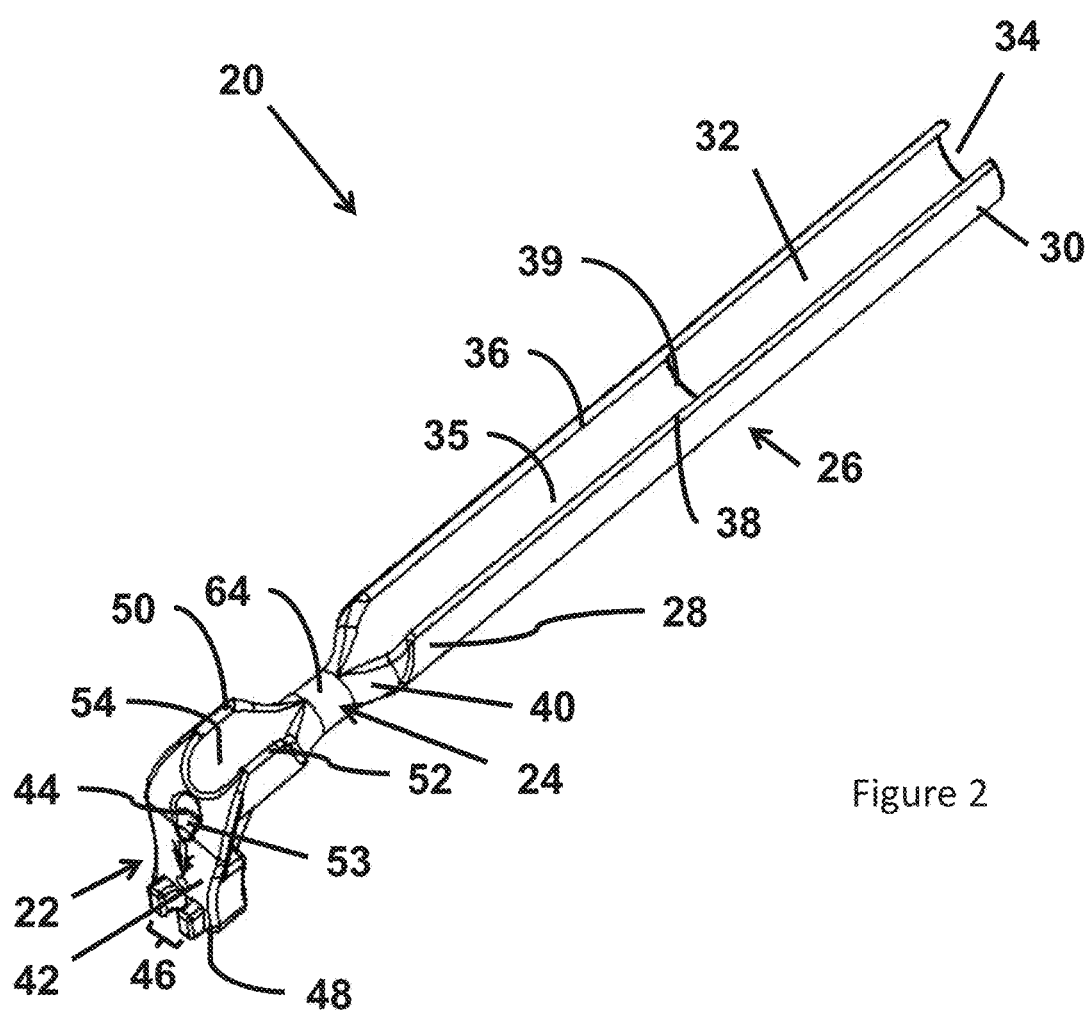
FIG. 2 is a perspective view of an adapter according to one embodiment.

Referring to FIG. 2, an adapter 20 is illustrated in accordance with one embodiment. In the illustrated embodiment, the adapter 20 includes a head 22, a neck 24 and a body 26. Further, the body 26 includes a proximal end 28 attached to the neck 24 and a distal end 30. The distal end 30 of the body 26 defines an opening 34. According to the illustrated embodiment, the body 26 includes an inner wall 35, a first annular wall 36 and a second annular wall 38. In one embodiment, the inner wall 35 extends parallel to the longitudinal axis of the adapter 20 and includes a distal end 39. In a further embodiment, the body 26 includes a cavity 32 formed in a distal region of the body 26 between the distal end 39 of the inner wall 35 and the opening 34. In addition, as illustrated, the proximal end 28 of the body 26 includes a tapered surface 40 that connects the body to the neck 24. According to the illustrated embodiment, the neck 24 has a constant diameter. As described herein, various embodiments include the neck 24 sized and configured to engage a seal included within the head of a trocar, for example, the head 12 of the trocar 10 illustrated in FIG. 1.

According to the illustrated embodiment, the head 22 includes a flange 42 that defines an opening 44 at a proximal end of a first lumen that is included in the adapter 20. In this embodiment, the flange 42 is oriented substantially perpendicular to the longitudinal axis of the adapter 20. However, depending on the embodiment, the head does not necessarily include a flange, or alternatively, includes a flange that is oriented other than perpendicular to the longitudinal axis. According to one embodiment, a set of jaws 46 is attached to the flange 42. Further, in one embodiment, the flange 42 includes a pair of wings 48 located on either side of the set of jaws 46. According to some embodiments, the head also includes a first annular wall 50, a second annular wall 52 and an interior wall 54. Further, in the illustrated embodiment, the head 22 includes a recess 53 in the flange 42 adjacent the opening 44. In one embodiment, the recess 53 provides space to allow a tube located in the first lumen 56 to more easily be bent ninety degrees so a portion of the tube can be secured in the jaws 46.

According to various embodiments, the adapter 20 includes a rigid or substantially rigid body manufactured, for example, from a molded plastic such as ABS or PVC. According to other embodiments, the adapter 20 is manufactured from a material selected from the group including polypropylene, nylon, Teflon, polyethylene, polycarbonate or a blended material including one or more of the preceding, alone or in combination with one another and/or other material(s).

Referring now to FIGS. 3A and 3B, a plan view of the proximal and distal ends, respectively, of the adapter 20 are illustrated. FIG. 3A illustrates a first lumen 56 with the opening 44 defined by the flange 42 located at a proximal end of the first lumen 56. Referring to FIG. 3B, the first lumen 56 extends axially from the head 22, through the neck 24 (see FIG. 2) and at least a portion of the body 26. According to these embodiments, the first lumen 56 terminates at the distal end 39 of the interior wall 35 included in the body 26.

According to various embodiments, the interior wall 54 and the interior wall 35 separate respective regions of the first lumen 56 from a second lumen 58. In the illustrated embodiment, the second lumen 58 is defined in the region of the head 22 by the interior wall 54, the first annular wall 50 and the second annular wall 52. Further, the illustrated embodiment includes an open region 60 located between the first annular wall 50 and the second annular wall 52. In the region of the body 26, the second lumen 58 is defined by the interior wall 35, the first annular wall 36 and the second annular wall 38. The illustrated embodiment includes an open region 62 located between the first annular wall 36 and the second annular wall 38.

According to the illustrated embodiment, the neck 24 includes an annular wall 64. Further, the first lumen 56 and the second lumen 58 extend axially through the neck 24. According to this embodiment, a region of the annular wall 64 couples the interior wall 54 to the interior wall 35, thereby forming a continuous wall to separate the first lumen 56 and the second lumen 58 from one another.

Each of FIGS. 3A and 3B illustrate an overall outline of the second lumen 58 in phantom. According to this embodiment, the region defined by the line drawn in phantom, the respective inner wall and the respective outer wall provide an approximate outline of the second lumen 58 when the adapter 20 is disposed within a trocar. In other alternate embodiments, the respective open regions 60 and 62 are replaced by a solid wall that completely encloses the second lumen 58. According to these embodiments, the area of the second lumen 58 is fixed whether the adapter 20 is disposed in a trocar or not.

Figure 4A:
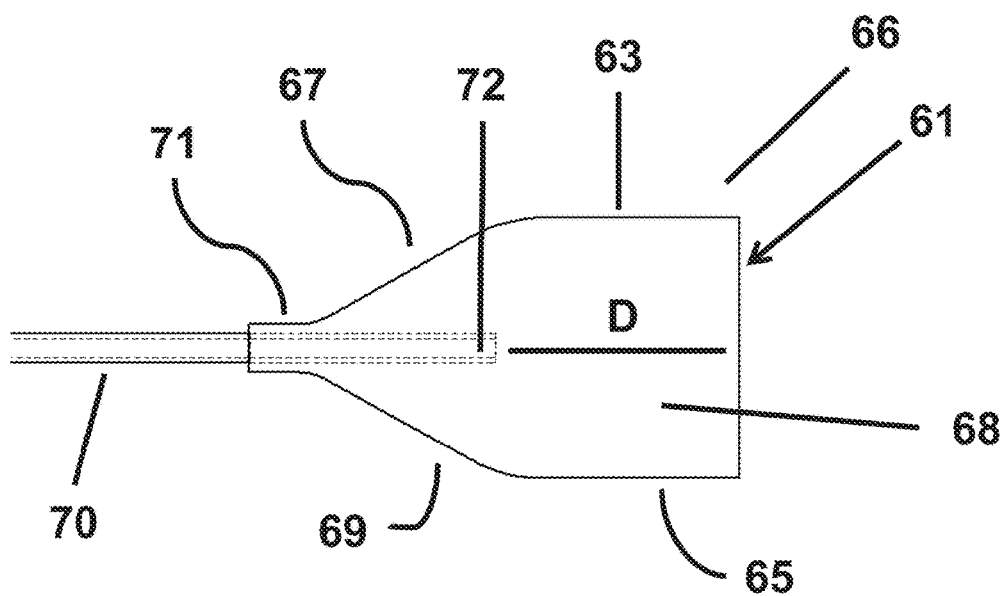
FIG. 4A is a plan view of a first side of the surgical sponge assembly according to one embodiment.
Figure 4B:
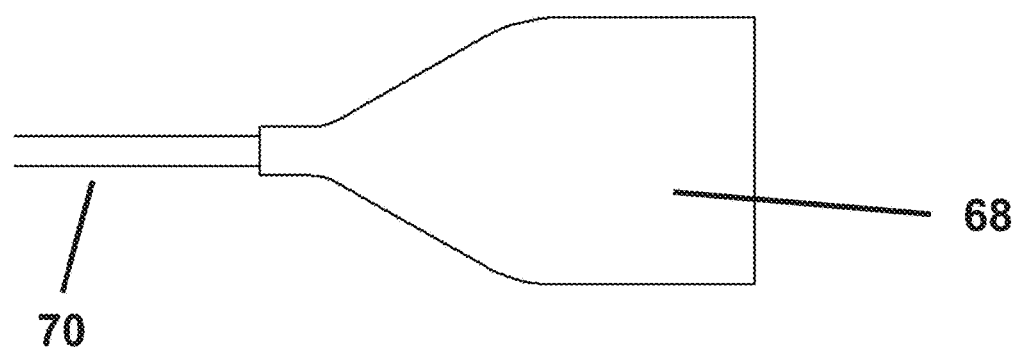
FIG. 4B is a plan view of a second side of the surgical sponge assembly illustrated in FIG. 4A.

Referring now to FIGS. 4A and 4B, a sponge assembly 66 is illustrated in accordance with one embodiment. According to this embodiment, the sponge assembly includes a sponge head 68 and a tube 70. The tube 70 includes a distal end 72 located in the sponge head 68 and proximal end (not illustrated) suitable for connection to a source of suction. The sponge head 68 includes a distal edge 61, a first side edge 63, a second side edge 65, a first tapered edge 67, a second tapered edge 69 and a junction 71.

According to the illustrated embodiment, each of the first side edge 67 and the second side edge 69 extend perpendicular to the distal edge 61 and substantially parallel to a longitudinal axis of the sponge assembly 66. The junction 71 is located at a proximal end of the sponge assembly where the tube 70 is fixedly attached to the sponge head 68. According to one embodiment, the first tapered edge 67 extends from the first side edge 63 to the junction 71. Further, the second tapered edge 69 extends from the second side edge 65 to the junction 71. The preceding provides the sponge head 68 with an overall construction that includes a v-shaped (or tapered region) located at the proximal end of the sponge head 68 between the tapered edges 67, 69 and a rectangle (or square shape) defined by the region between the v-shaped region, the side edges 63, 65 and the distal end 61. According to one embodiment, the tube 70 is secured to the sponge head 68 at the junction 71.

In various embodiments, the sponge assembly 68 includes a layered construction. In further embodiments, the various layers are coupled to one another along at least a portion of their respective edges, for example, by a polymer rib. In alternate embodiments, other approaches are employed to assemble the multiple layers in the sponge assembly 66. The construction details for one embodiment are provided below. However, in general, the sponge head 68 can include one or more types of absorbent material and optionally one or more non-absorbent layers arranged to facilitate the use of both suction and absorption. In some embodiments, the preceding is achieved in a configuration suitable for use with the adapter 20.

According to various embodiments, the attachment of the layers to one another can be made around all outside edges of the sponge head 68. In other embodiments, one or more edge regions may not be employed in securing the layers to one another. For example, in the illustrated embodiment, the layers are secured to one another at the junction 71, along each of the tapered edges 67, 69 and along each of the side edges 63, 65. In some embodiments, the layers are secured only in a discrete spot or spots along one or more edge. For example, one or more dots of adhesive can be applied rather than a bead of adhesive. According to one embodiment, the layers are not secured to one another along the distal edge 61. According to another embodiment, the layers are secured to one another along the distal edge 61 only in the center of the edge 61. According to this embodiment, a centrally located point-of-attachment provides the sponge head 68 with a neater appearance while also assisting in the folding of the sponge head when moved into a retracted position within the adapter 20.

FIGS. 5A-5E illustrate the sponge head 68 in accordance with one embodiment in which a layered construction is employed. In the illustrated embodiment, the sponge head 68 includes a non-absorbent layer 74, a first absorbent layer 76 and a second absorbent layer 78. According to this embodiment, a rib 80 is located around at least a portion of a periphery of the sponge head 68 to secure the layers 74, 76, 78 in the overall assembly. Depending on the embodiment, the construction of the rib 80 can differ provided that the result securely retains the layers in a unitary construction that will not accidently disassemble into component parts when applied in a surgical procedure, for example, a minimally invasive surgical procedure.

According to some embodiments, the rib is formed of a polymer that is applied in an injection process, for example, an injected silicone rib. In one embodiment, a two-part silicone is employed in a low pressure injection process where the silicone cures in place to form the rib. According to other embodiments, a heated polymer or a one part curing polymer is employed. As illustrated in FIGS. 4A and 4B, the rib is located along the two opposing edges of the sponge head 68. The two edges converge at the junction 71 located at the proximal end of the sponge head 68. Referring to FIGS. 4A and 4B, the tube 70 is secured to the sponge head 68 by the rib at the junction 71.

Figure 5A:
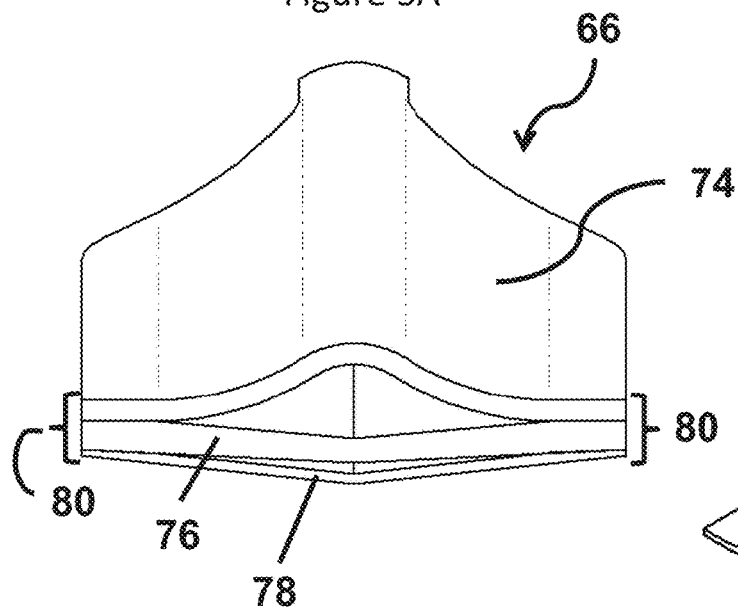
FIGS. 5A-5E are views of the construction of the surgical sponge assembly illustrated in FIG. 4A.
Figure 5B:
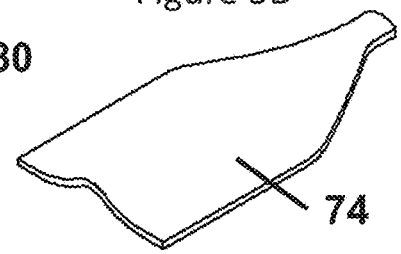

According to the embodiment illustrated in FIG. 5B, the non-absorbent layer 74 is a transparent film, for example, a transparent silicon film. In addition to being non-absorbent, the layer 74 can also be provided in a material that does not breathe. An advantage of the preceding is that the suction force provided by the sponge assembly 66 can be focused in a particular direction. For example, with the distal end 72 of the sponge located as illustrated in FIG. 4A suction will only be applied to tissue in the vicinity of the distal end 61 and the side of the sponge head 68 opposite the non-absorbent layer 74. The preceding provides a form of directional suction that can prevent damage to sensitive tissue in the region of the sponge assembly 66. Depending on the embodiment, the non-absorbent layer 74 is manufactured from material selected form the group including transparent silicone film, PVC, polyethylene, polypropylene, Buna rubber, polycarbonate, Teflon, nylon and thermoplastic elastomer.

Figure 5C:
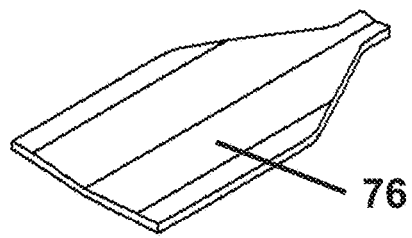

Further, in some embodiments, the first absorbent layer 76 is located immediately adjacent the non-absorbent layer 74. As illustrated in FIG. 5C, the first absorbent layer 76 is medical gauze suitable for absorbing a relatively substantial amount of liquid for a given surface area of the first absorbent layer 76. In a further embodiment, the first absorbent layer 76 is manufactured of cotton in an open (or loose) weave to provide greater absorbency. Other styles and types of gauze or other absorbent material can be employed depending on the embodiment.

Figure 5D:
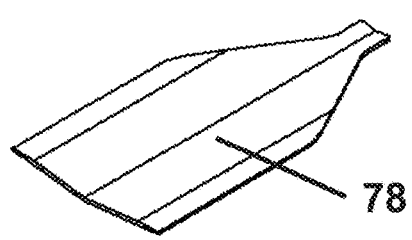
Figure 5E:
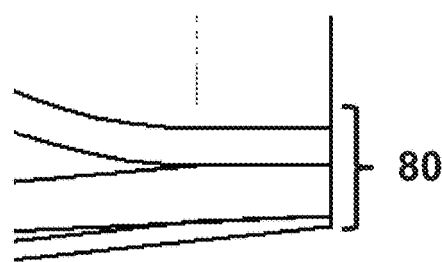

In the illustrated embodiment, the second absorbent layer 78 is located immediately adjacent the first absorbent layer 76 on a side opposite the non-absorbent layer 74. As illustrated in FIG. 5D, the second absorbent layer 78 is a medical tissue. In various embodiments, the medical tissue is manufactured of cotton using a close weave. In other embodiments, the second absorbent layer 78 is a nonwoven pad manufactured in a process in which the absorbent fibers are pressed together. These embodiments can provide an advantage of minimizing or entirely eliminating the production of lint by the sponge assembly 66 during a surgical procedure in which it is employed. For example, the tight construction of the second absorbent layer 78 resists shedding lint. In addition, the location of the second absorbent layer 78 as the outside layer retains any lint that might be shed from the first non-absorbent layer within the sponge head 68. According to one embodiment, the second absorbent layer 78 is manufactured of synthetic fibers such as polyester, rayon, or blend of synthetic fibers.

Various embodiments of the sponge head 68 provide further advantages in surgical procedures. For example, in some embodiments, the relatively tight weave of the second absorbent layer creates a partial flow restriction. When employed with a sponge head 68 that includes an open or partially open distal end 61 the partial flow restriction results in the majority of the liquid that is drawn into the tube 70 being drawn into the sponge head 68 via the distal end 61. This focused suction acts to keep the first absorbent layer from saturating because the majority of air drawn into the tube 70 is drawn through the first absorbent layer 76. The result is that the first absorbent layer can maintain a higher rate of absorption without saturating because a greater amount of liquid that is absorbed by the layer 76 is drawn into the tube 70. In some other embodiments that can be independently implemented or combined with the preceding, a centrally located point-of-attachment on the distal edge 61 is provided and an increased rate of suction and clearing through the open edge of the sponge head 68 is achieved by providing a partial restriction along an otherwise open edge.

In various embodiments where the second absorbent layer 78 provides a flow restriction, the distal end 61 being at least partially open also facilitates operation of the sponge assembly 66 because the open end assures sufficient flow to adequately clear fluids. According to these embodiments, the sponge head 68 provides a multi-flow rate operation including at least a first surface region that allows a restricted air flow (for example, the second absorbent layer 78) between an exterior surface of the sponge head 68 and an interior region of the sponge head 68 and a second surface region (for example, the first absorbent layer 76) that allows unrestricted air flow between the exterior surface of the sponge head 68 and the interior region of the sponge head 68. In one embodiment, in addition to the preceding, the sponge head 68 also includes a non-breathable exterior surface (for example, the non-absorbent layer 74) that does not allow any airflow between the exterior surface of the sponge head 68 and the interior region of the sponge head 68.

According to one embodiment, the sponge assembly 66 is manufactured by cutting a section of each of the non-adhesive layer 74, the first absorbent layer 76 and the second absorbent layer 78, respectively, into the appropriate shape (s). The preceding operation can be completed in an automated process or by hand, for example, using a guide or template. The layered components are set in an injection mold with the tube 70 located between the non-adhesive layer 74 and the first absorbent layer 76. The axial position of the tube 70 is adjusted to place the distal end 72 of the tube 70 a distance D (see FIG. 4A) from the distal end 61 of the sponge head 68. With the mold assembled, the heated polymer is injected into the mold cavity to form the rib 80. As described above, the amount of the edge region in which the rib 80 is formed can vary depending on the embodiment. As a result, the mold can be designed to locate the rib around all or some portion of the sponge head 68.

Figure 6A:
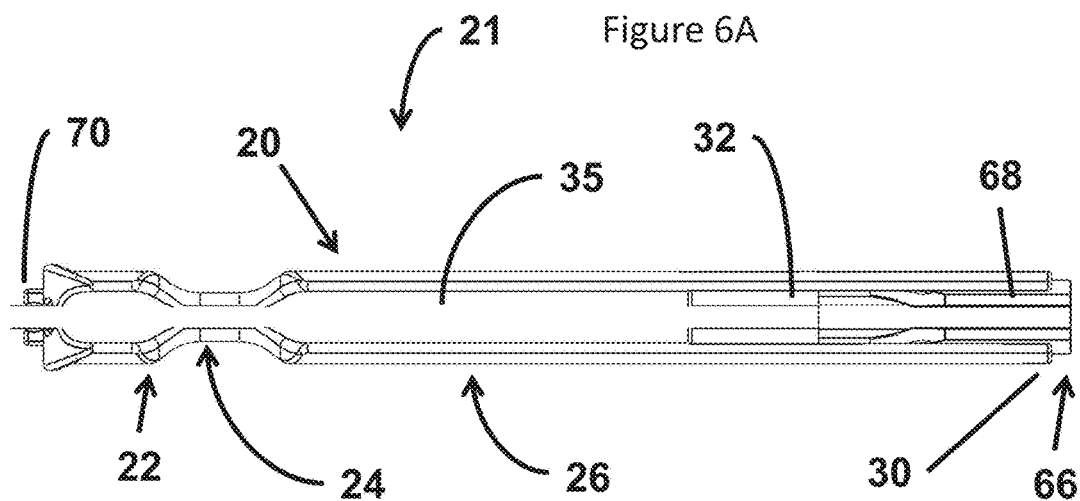
FIG. 6A is a plan view of a system including an adapter and a surgical sponge assembly in accordance with one embodiment.
Figure 6B:
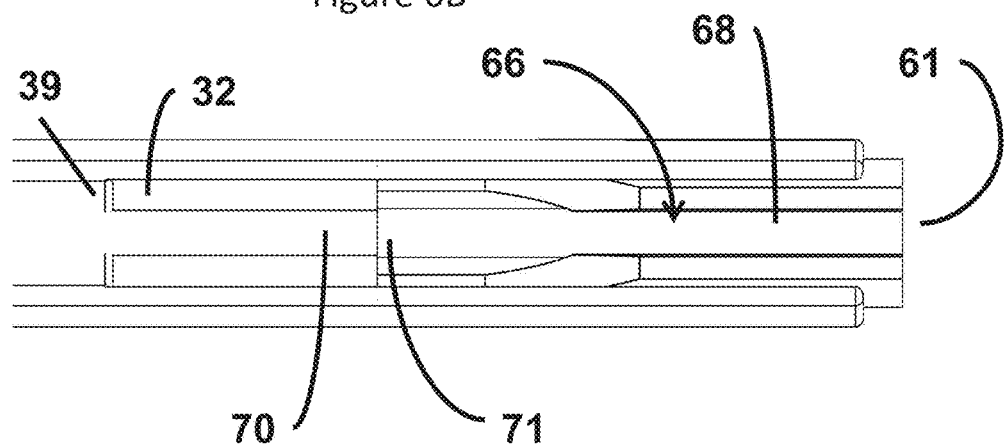
FIG. 6B is a plan view of the distal end of the system illustrated in FIG. 6A.

FIGS. 6A and 6B illustrate the sponge assembly 66 disposed in the adapter 20. According to various embodiments, the sponge assembly 66 and the adapter 20 are provided in a system 21 employed in a surgical procedure. In the illustrated embodiment, the tube 70 is located in the first lumen 56. The adapter 20 is oriented such that the second lumen 58 can be viewed extending axially from the head 22, across the neck 24 and along the body 26 from the flange 42 (which in this embodiment is located the proximal end of the adapter 20) to the distal end 30 of the body (which in this embodiment is located at the distal end of the adapter 20).

According to various embodiments, the adapter 20 includes the cavity 32 for storage of at least a part of the sponge head 68. In these embodiments, the sponge assembly 68 can be positioned in at least two positions: a retracted position in which all or a substantial portion of the sponge head 68 is retracted within the body 26 as illustrated in FIG. 6A; and an extended position in which all or a substantial portion of the sponge head 68 is located beyond the distal end 30 of the body. In some embodiments, the axial movement of the sponge assembly 66 occurs when a user grips a portion of the tube 70 located beyond the proximal end of the adapter 20 and moves the tube in either the proximal or the distal direction. Additionally, an operator can also employ another surgical tool inserted within the patient via a different port to grasp the distal end 61 and withdraw the sponge head 68 beyond the distal end 30 of the body and place the head as needed within the surgical site.

In one embodiment, the entirety of the sponge head 68 is located within the body 26 in the fully retracted position. In an alternate embodiment, a portion of the sponge head 68 remains outside the distal end 34 of the body 26 in the fully retracted position.

According to various embodiments, the system 21 provides an improved method of disposing a sponge in a surgical area within a patient via a port. The size of ports used in minimally invasive surgery often make it difficult for medical professionals to try and "snake" a sponge through the relatively small port into the surgical area. The system 21 allows a sponge stored in a retracted position to easily move through the port when the adapter 20 is inserted in the trocar 10. The user need only slide the system 21 into the trocar 10 to locate the sponge head 68 at the distal end 17 of the cannula 14.

FIG. 6B illustrates a view of the cavity 32 with the sponge assembly 66 in the retracted position. According to the illustrated embodiment, the distal end 61 of the sponge head 68 remains located outside the cavity 32 with the sponge assembly 66 in a position that is close too but not yet in a fully retracted position. According to some embodiments, the junction 71 is located within the cavity 32 with the sponge assembly 66 in the fully retracted position. According to other embodiments, all or a portion of the junction 71 is withdrawn into a distal end of the first lumen 56. According to these embodiments, the distal end 61 of the sponge head 68 is located within the cavity 32 with the sponge assembly 66 in the fully retracted position. In other embodiments, the distal end 39 of the inner wall 35 is located further from the proximal end 30 of the body 26 to allow the sponge head 68 to be retracted into the cavity 32 such that the distal end 61 is fully inside the cavity 32.

In various embodiments, the sponge head 68 is constructed with a flexible set of materials that allow the sponge head 68 to automatically fold into a smaller size when drawn within the cavity 32. In further embodiments, the sponge head 68 includes one or more compressible materials that allow the sponge head 68 to compress when drawn within the cavity 32. In various embodiments, the sponge head 68 has an overall flexible and resilient construction that allow the sponge head 68 to expand back to its original shape when it is moved to the extended position outside of the adapter 20.

In some embodiments, the overall shape of the sponge head 68 is designed to facilitate a user's ability to withdraw the sponge head 68 within the cavity 32 to the retracted position. For example, as illustrated in FIGS. 4A and 4B the sponge head 68 includes the first tapered edge 67 and the second tapered edge 69 that join one another at the junction 71. According to this embodiment, the overall tapered shape of the proximal end of the sponge head 68 avoids creating the type of interference that would be encountered if the overall shape of the sponge head was a parallelogram. This allows the sponge head 68 to easily be retracted within the cavity 32 using a minimum amount of force. According to these embodiments, the durability of the sponge head 68 is improved.

In various embodiments, the adapter 20 is employed to convert a single lumen trocar to a multi-lumen trocar to allow the use of the sponge assembly 66 via the trocar in combination with different surgical tools that can be simultaneously employed using the same trocar. According to these embodiments, the sponge assembly is deployed via the first lumen 56 while the other surgical tool(s) are deployed via the second lumen 58.

Figure 7:
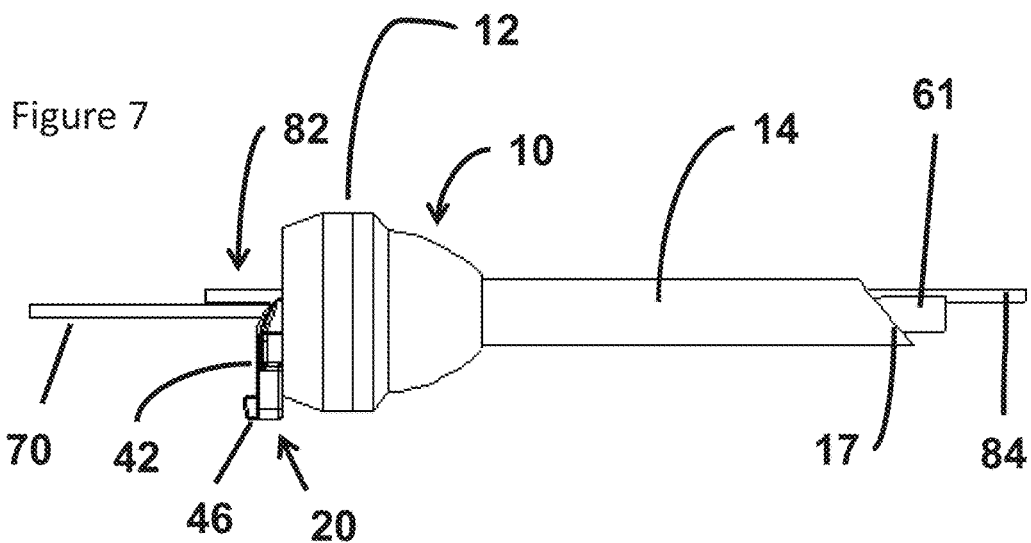
FIG. 7 is a plan view of the system illustrated in FIG. 6A inserted within a trocar in accordance with one embodiment.

Referring to FIG. 7, the adapter 20 is shown in combination with the trocar 10. A conventional trocar such as the trocar 10 provides a single lumen that extends axially through the head 12 and the cannula 14 to the distal end 17 of the cannula 14. As illustrated, the adapter 20 is located within the trocar 10 such that the flange 42 abuts the head 12 and the distal end 61 of the sponge head 68 extends just beyond the distal end of the trocar. Further, FIG. 7 illustrates the adapter with the sponge assembly 66 in the retracted position such that the sponge head 68 is folded inside the adapter 20. The tube 70 extends out the proximal end of the trocar 10 with the adapter 20 installed in the trocar 10.

With the adapter 20 located in the trocar 10, a surgical tool 82 can be simultaneously deployed in a surgical procedure in combination with the sponge assembly 66. FIG. 7A illustrates one such example in which the surgical tool 82 is inserted in the proximal end of the trocar 10 in the second lumen 58 provided by the adapter 20. The surgical tool can then be moved axially until a distal end 84 of the tool is disposed beyond the distal end of the trocar 10.

Figure 8:
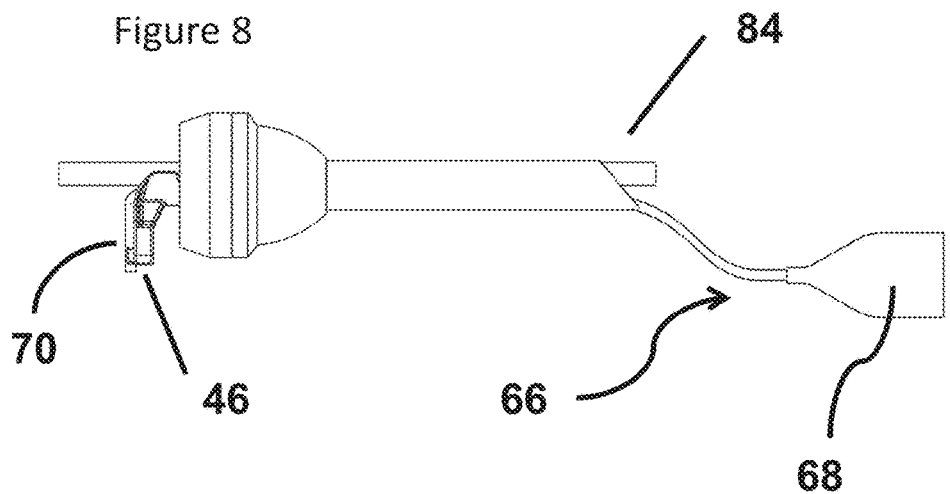
FIG. 8 is a plan view of the system and trocar illustrated in FIG. 7 with the surgical sponge extended beyond a distal end of the trocar.

The configuration of the adapter 20 and the sponge assembly 66 also allows an axial movement of the sponge assembly 66 during use. Referring to FIG. 8, the sponge assembly 66 is moved in a distal direction relative to its position in FIG. 7. The axial movement locates the sponge assembly 66 in an extended position with the sponge head 68 extended beyond a distal end of the trocar 10. In some embodiments and depending on the application, a portion of the tube 70 can also be moved beyond the distal end of the trocar 10 when the sponge assembly 66 is deployed. As described above, the jaws 46 can be employed to temporarily secure the tube in place, for example, to temporarily prevent further axial movement of the sponge assembly 66 once a desired axial position of the sponge head 68 is established. FIG. 8 illustrates the tube 70 retained in the jaws 46 in accordance with one embodiment.

Depending on the embodiment, a system including the adapter 20 and sponge assembly 66 is employed in a surgical procedure that can include endoscopic surgery including natural orifice transluminal endoscopic surgery, trauma surgery, craniomaxillofacial surgery and various types of robotic surgery. Further, the second lumen 58 provided by the adapter 20 can be employed with a variety of conventional surgical tools provided that their outside diameter allows the surgical tool to fit within the second lumen 58. For example, surgical tools such as cameras, graspers, cutting tools, cautery tools, irrigation tools and suction equipment.

Figure 9:
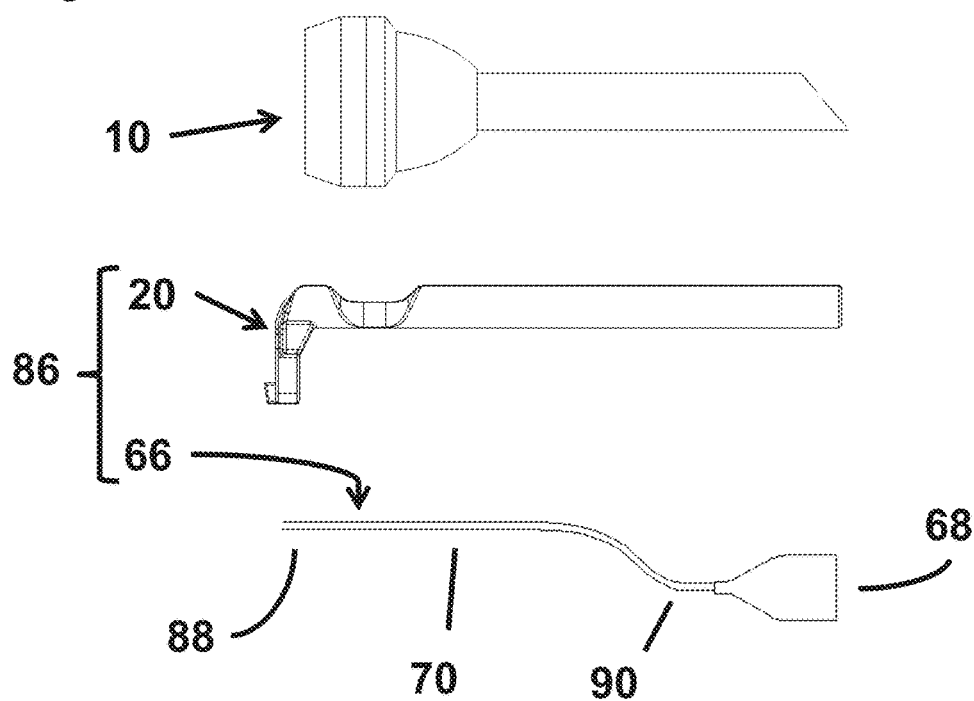
FIG. 9 is a plan view of the adapter, surgical sponge assembly and trocar illustrated in FIG. 7 disassembled from one another.

Referring to FIG. 9, a system 86 including the adapter 20 and the sponge assembly 66 is illustrated in accordance with one embodiment. The system 86 can be employed with the trocar 10 in accordance with various embodiments. According to the illustrated embodiment, the sponge head 68 lays flat when it is not located within the adapter 20. According to some embodiments, the system 86 is provided in the form of a kit including the adapter 20 and the sponge assembly 66. Before employing the system 86, the adapter 20 and the sponge assembly 66 are assembled together. In the illustrated embodiment, a proximal end 88 of the tube 70 is slid within the first lumen 56 from the distal end of the adapter 20. The user can hold a distal end 90 of the tube 70 and continue to apply an axial force in the direction of the head 22 of the adapter 20 until the proximal end 88 extends beyond the proximal end of the first lumen 56 in the vicinity of the flange 42. The user can then hold the proximal end 88 of the tube 90 and pull the tube in a proximal direction to draw the sponge head 68 into the opening 34. Further axial movement in the proximal direction moves the sponge head 68 into the cavity 32. According to some embodiments, the flexible nature of the sponge head 68 allows the sponge head to fold along its axis as it is drawn into the cavity 32, for example, as illustrated in FIG. 6B. As illustrated in FIG. 7, the fully assembled kit can be deployed in a trocar by inserting from the proximal end until the underside of the flange 42 abuts the head 12 of the trocar 10.

According to some embodiments, a balance between the flexibility and the stiffness of the tube 70 is established to allow the sponge head 68 to be placed in the surgical site and maintain its position. In contrast, a tube that is too flexible makes it difficult to push the sponge head 68 from the retracted position to the extended position. A tube that is too stiff makes it difficult to keep the sponge head 68 in the desired location in the surgical site because the tube can limit the range of motion. As a result, the tube tends to repeatedly return the sponge head 68 to one location in the surgical site.

Figure 10:
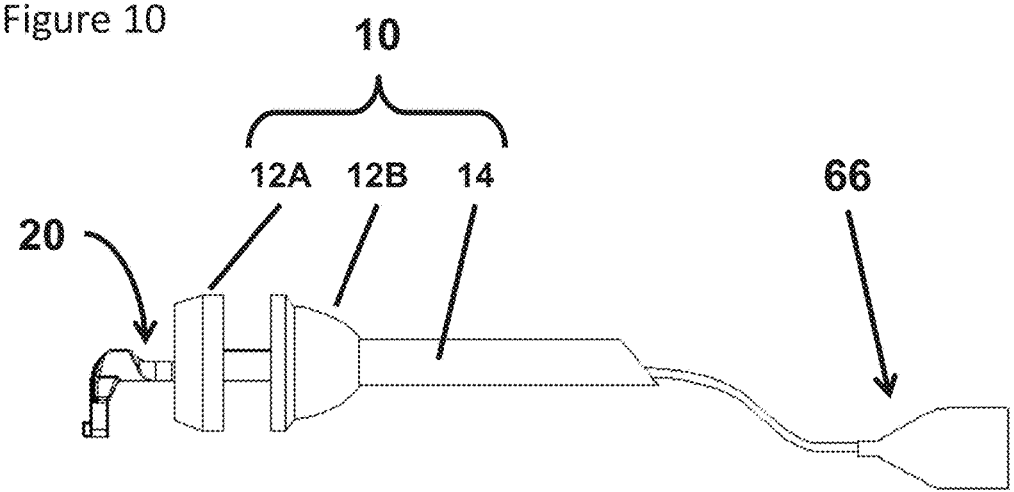
FIG. 10 is a partially exploded view of the adapter, surgical sponge assembly and trocar illustrated in FIG. 7.

Referring now to FIG. 10, a partially disassembled trocar 10 and system 86 are illustrated. According to the illustrated embodiment, the head includes an upper region 12A and a lower region 12B that are snap fit together. In FIG. 10, the adapter 20 is partially extended out a proximal end of the trocar 10, the sponge assembly 66 is partially withdrawn out a distal end of the trocar, and the head 12 is disassembled into the upper region 12A and the lower region 12B.

Figure 11:
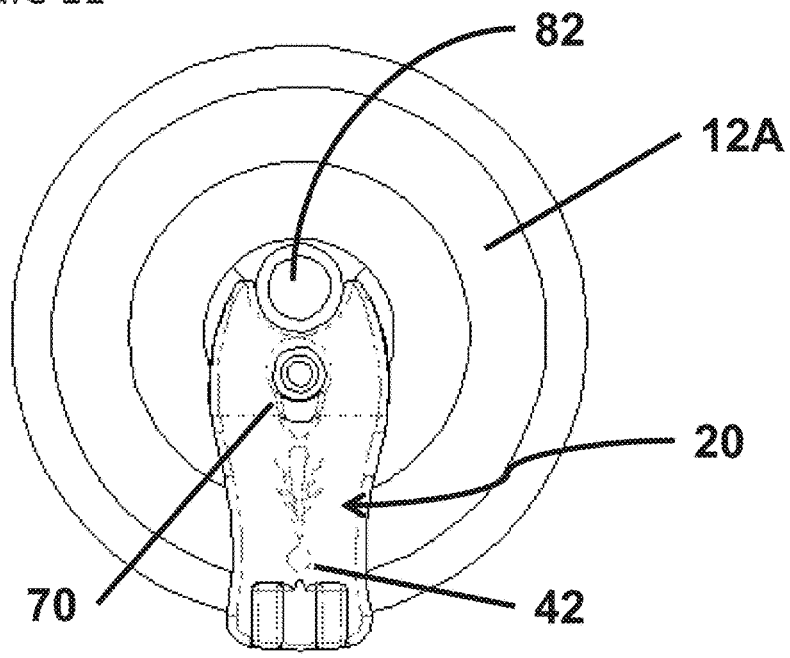
FIG. 11 is a plan view of a proximal end of the adapter, surgical sponge assembly and trocar illustrated in FIG. 7.
Figure 12:
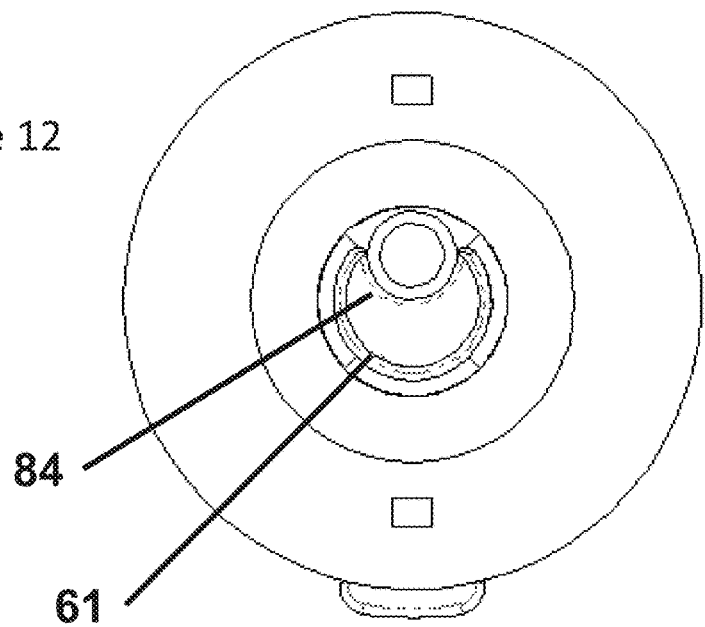
FIG. 12 is a plan view of a distal end of the adapter, surgical sponge assembly and trocar illustrated in FIG. 7.

FIG. 11 illustrates the upper region 12A with the surgical tool 82 and the system 86 disposed within the trocar 10 according to one embodiment. In this view, a proximal end of the surgical tool 82, the proximal end of the adapter 20 and the tube 70 can also be seen. In FIG. 12, the distal end of the trocar 10 is viewed according to one embodiment. In this view, the distal end 84 of the surgical tool 82, and the distal end 61 of the sponge head 68 can also be seen with the sponge assembly 66 in the retracted position.

Figure 13:
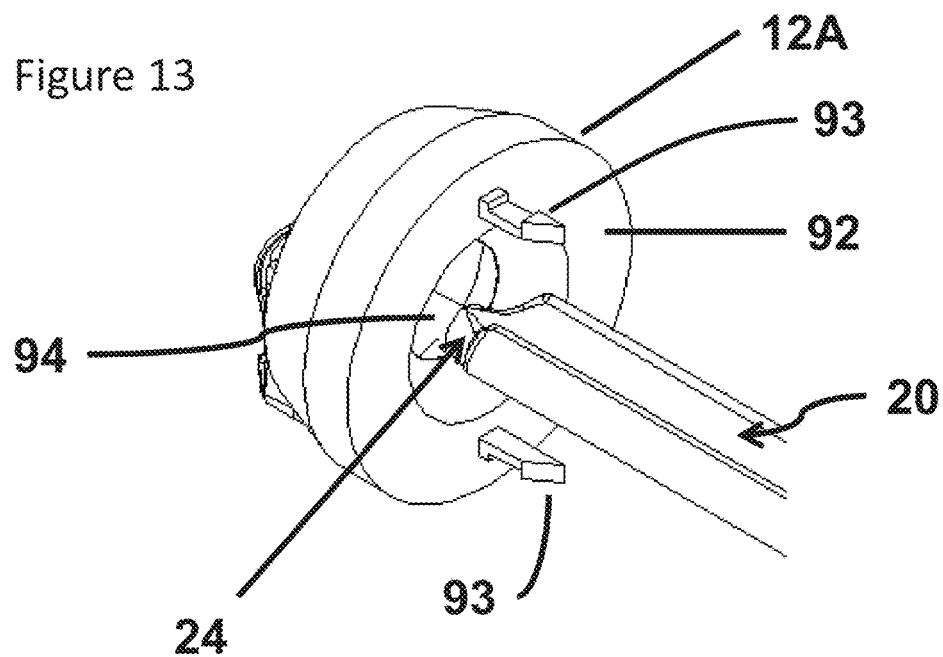
FIG. 13 is an isometric view of the adapter illustrated in FIG. 2 inserted within a portion of the trocar illustrated in FIG. 1A.

Referring now to FIG. 13, a perspective view of the upper region 12A of the head 12 is illustrated with the upper region 12A disconnected from the lower region 12B. FIG. 13 illustrates an underside 92 of the upper region 12A, snaps 93, a seal 94 and the adapter 20 inserted within the upper region 12A such that the neck 24 is engaged with the seal 94. In one embodiment, the snaps 93 are employed to secure the upper region 12A to the lower region 12B of the head 12. Further, the sealing engagement of the neck 24 and the seal 94 illustrated in FIG. 13 is maintained with the upper region 12A attached to the lower region 12B.

Often, internal surgical sites are held open by applying a positive pressure within the patient. The seal 94 included in the trocar is intended to minimize the loss of positive pressure and consequently limit the amount of make-up air required to maintain the positive pressure. Leaks can also deflate the surgical site which changes the surgeon's visual references. As a result, completion of surgical procedures can be delayed as sufficient positive pressure is returned to the surgical site The seal 94 is also engaged with a surgical tool that is inserted via the trocar. However, the seal increases the difficulty of disposing surgical sponges within the surgical site. Generally, the seal 94 is designed to sealing engage objects inserted with the trocar 10 that are cylindrically shaped.

In some embodiments, the neck 24 of the adapter 20 is designed to sealing engage the seal 94 with the system 21 disposed within the trocar 10. In further embodiments, the neck 24 provides a cylindrical shape with an outside diameter sized to sealing engage the seal 94. In these embodiments, the seal is maintained during operation of the system including extension of the sponge head 68 to a surgical site and the retraction of the sponge head 68 within the cavity 32.

Figure 14:
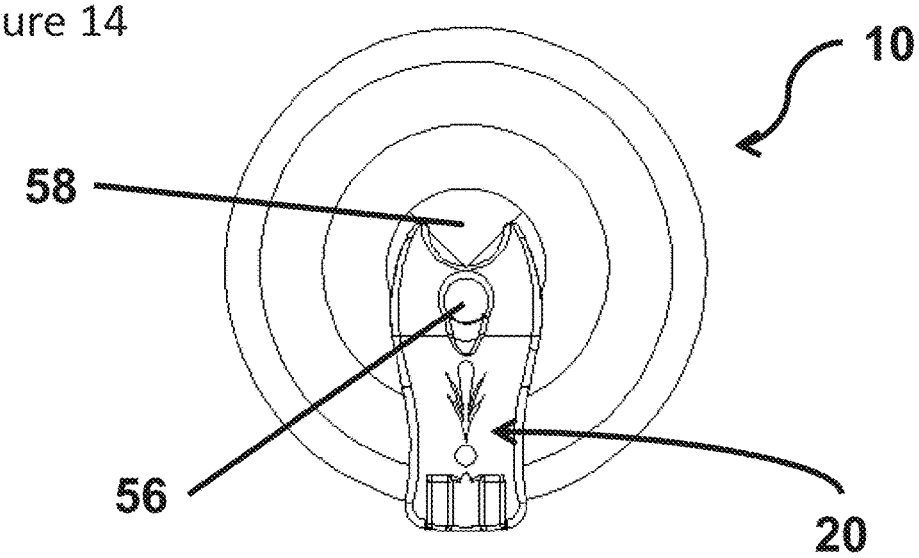
FIG. 14 is a plan view of the proximal end of the adapter and trocar illustrated in FIG. 13.

FIG. 14 illustrates a view of the head 12 and the adapter 20 with the adapter fully seated in the trocar to complete the sealing engagement illustrated in FIG. 13. The first lumen 56 and the second lumen 58 are illustrated in an empty state in FIG. 14 because neither the sponge assembly 66 nor the surgical tool 82 are shown. According to some embodiments, the adapter 20 is provided for use without the sponge assembly 66. In these embodiments, the adapter 20 is employed to provide two lumens for use by separate surgical tools where neither surgical tool includes a sponge. In some embodiments, the two lumens 56, 58 are substantially parallel to one another and parallel to the longitudinal axis of the adapter 20. Further, these embodiments may be configured to provide the two lumens 56, 58 the full length of the adapter 20. That is, the adapter 20 may not include the cavity 32. Further, embodiments that include the sponge assembly can also be constructed similarly to provide complete separation of the two lumens 56, 58.

As described above, the neck 24 of the adapter 20 is designed to sealing engage the seal 94 with the system 21 disposed within the trocar 10. According to some embodiments, an overall sealing engagement is maintained when a surgical tool is inserted with in the second lumen 58 because the adapter 20 including the neck 24 is sized and shaped to provide parallel cylindrically shaped lumens 56, 58 with the system 21 disposed within the trocar 10 while maintaining a seal at the neck 24. For example, see FIGS. 3A, 3B and 14 which each illustrate the overall cylindrical shape of the first lumen 56 and the second lumen 58.

Figure 15:
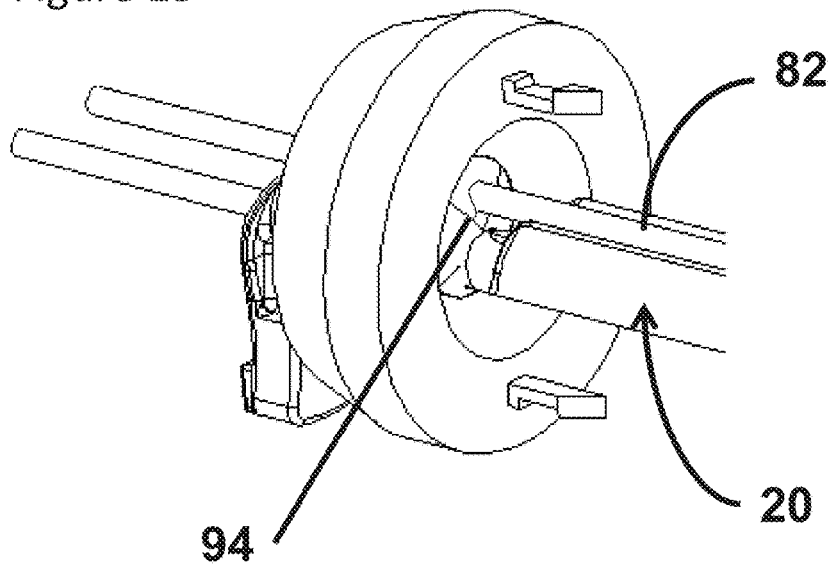
FIG. 15 is an isometric view of the adapter illustrated in FIG. 2 and a surgical tool each inserted within a portion of the trocar illustrated in FIG. 1A.

Referring now to FIG. 15, a perspective view of the upper region 12A is provided in which both the surgical tool 82 and the adapter 20 are inserted through the lumen in the upper region 12A. According to the illustrated embodiment, a sealing engagement is provided between the seal 94 and each of the adapter 20 and the surgical tool 82. Further, the seal illustrated in FIG. 15 is maintained with the surgical tool 82 and the adapter disposed in the fully assembled trocar 10. According to some embodiments, the first lumen 56 provided by the adapter is available for use by the sponge assembly 66 and the second lumen 58 provides the lumen employed with the surgical tool 82. As a result, the adapter 20 converts the single lumen provided in the conventional trocar to a dual lumen allowing each of the sponge assembly 66 and the surgical tool 82 to be employed in a surgical procedure via the respective lumens 56, 58. In one embodiment, second lumen 58 is provided by a combination of the adapter 20 and an inner wall of the lumen of the trocar.

Figure 16:
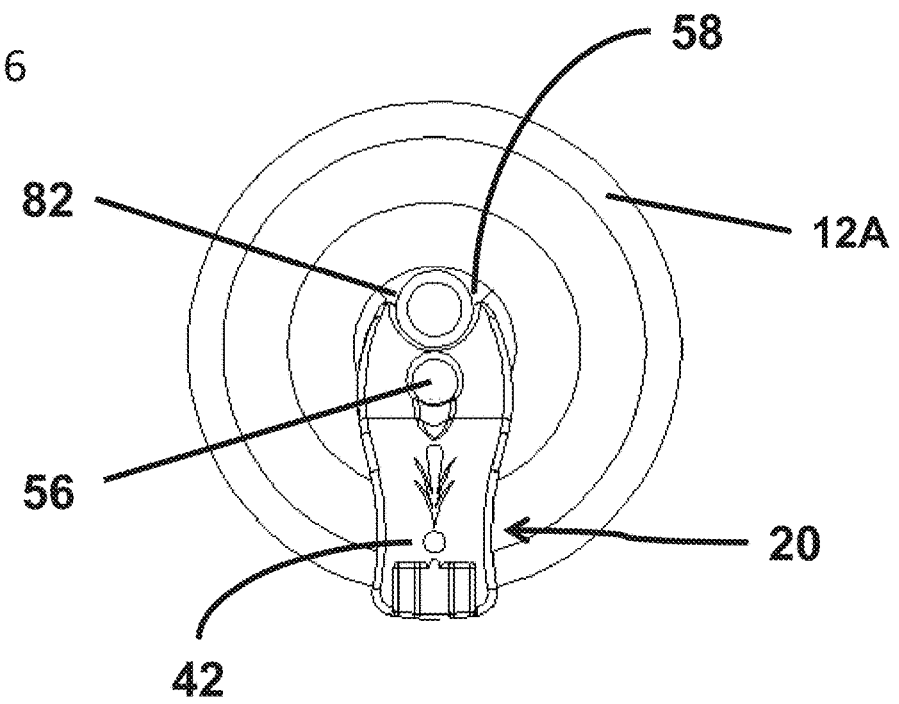
FIG. 16 is a plan view of the proximal end of the adapter, surgical tool and trocar illustrated in FIG. 15.

FIG. 16 illustrates the adapter 20 inserted in the trocar such that an underside of the flange 42 abuts the proximal end of the head 12 and locates the neck 24 in sealing engagement with the seal 94 as illustrated in FIGS. 13 and 15. As illustrated, in FIGS. 7 and 8 the sponge assembly 66 can be included and operated as shown and described herein.

While the adapter 20 is primarily illustrated and described with reference to a two-lumen device, for example, the lumens 56 and 58, other configurations may be employed. For example, in one embodiment, the body does not include the second lumen 58. Instead, the adapter 20 includes only the first lumen 56. According to this embodiment, the adapter 20 is employed to dispose the sponge assembly 66 within the cannula 14 such that the assembly 66 can be deployed from the distal end 17.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An apparatus for use in combination with a surgical sponge assembly and a trocar including a cannula having an interior wall, the surgical sponge assembly including a suction tube coupled to a sponge head, the apparatus comprising:
   a body configured to insert within the cannula and including a proximal end, a distal end, a first lumen and a second lumen that join one another to form a cavity defined by an annular wall, a longitudinal axis, an interior wall that extends from the proximal end of the body to the cavity, a first exterior wall that extends around a first portion of the circumference of the apparatus, a second exterior wall that extends around a second portion of the circumference of the apparatus, and a gap formed between the first exterior wall and the second exterior wall extending parallel to the longitudinal axis at least a length of the cavity,
   wherein the first lumen and the second lumen are separated from one another by the interior wall included in the body,
   wherein, with the body inserted within the cannula, the annular wall defining the cavity includes at least portion of each of the interior wall included in the cannula, the first exterior wall and the second exterior wall, respectively,
   wherein the first lumen is sized and configured to allow an axial movement of the suction tube within the first lumen, the cavity configured to store at least a portion of the sponge head,
   wherein the apparatus is configured to allow the surgical sponge assembly to be moved from a retracted position in which at least a portion of the sponge head is stored within the cavity and an extended position in which at least some of the portion of the sponge head stored within the cavity in the retracted position is located beyond the distal end of the body, and
   wherein the apparatus is configured to be inserted within the cannula with the sponge head stored in the cavity in the retracted position.

2. The apparatus of claim 1, the trocar including a head coupled to the cannula and a seal located within the head, the apparatus further comprising:
   a neck coupled to the proximal end of the body and having an outside diameter selected to engage the seal with the body disposed within the cannula.

3. The apparatus of claim 2, further comprising:
   a flange coupled to the proximal end of the body via the neck, the flange defining a first opening and a second opening, the flange configured to remain outside the cannula with the body disposed within the cannula.

4. The apparatus of claim 2, wherein the first lumen extends from the first opening through the neck to a third opening located at a distal end of the interior wall included in the body, and
   wherein the second lumen extends from the second opening through the neck to the distal end of the interior wall included in the body, the second lumen configured to receive a surgical tool.

5. The apparatus of claim 1,
   wherein the first exterior wall and the second exterior wall extend axially from the proximal end of the body to the distal end of the body, and
   wherein the gap formed between the first exterior wall and the second exterior wall extends from the proximal end of the body to the distal end of the body.

6. The apparatus of claim 3, further comprising jaws coupled to the flange,
   wherein the jaws are configured to retain the suction tube via an interference fit.

7. The apparatus of claim 6, wherein the flange includes a planar face oriented at substantially ninety degrees to a longitudinal axis of the apparatus, and wherein the jaws are located on the planar face of the flange.

8. A kit for use with a trocar assembly including a seal and a cannula, the kit comprising:

a surgical device including a tube coupled to a surgical sponge; and an adapter including a first lumen and a second lumen, the adapter including a body sized and configured to be received within the cannula, the first lumen and the second lumen extending from a proximal end of the adapter to a cavity located within the body, wherein the first lumen is sized such that the tube can be slidably disposed within the first lumen, wherein the cavity is sized such that at least a portion of the surgical sponge can be slidably disposed within the cavity between a retracted position in which at least a portion of the sponge is located within the cavity and an extended position in which the surgical sponge is located beyond the distal end of the adapter, and wherein, with the body inserted within the cannula, the cavity is defined by exterior walls included in the adapter in combination with an interior wall of the cannula.

9. The kit of claim 8, further comprising jaws located at the proximal end of the adapter, the jaws configured to retain the tube to maintain an axial position of the surgical device with the tube retained in the jaws.

10. The kit of claim 8, wherein the surgical sponge includes a multi-layered construction that is flexible and resilient such that the surgical sponge folds for storage within the cavity and unfolds to form a substantially planar shape when located beyond the distal end of the adapter.

11. The kit of claim 8, wherein the adapter includes a neck located between the proximal end of the adapter and the body, and wherein the neck includes a tapered construction to form a seal when engaged with the seal included in the trocar when the adapter is located within the cannula.

* * * * *